United States Patent
Dittrich et al.

(10) Patent No.: US 6,447,502 B1
(45) Date of Patent: Sep. 10, 2002

(54) PROTECTIVE CAP FOR MEDICAL HF INSTRUMENTS

(75) Inventors: Horst Dittrich, Immendingen; Uwe Bacher, Tuttlingen, both of (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/451,017

(22) Filed: Nov. 29, 1999

Related U.S. Application Data

(63) Continuation of application No. PCT/EP98/03064, filed on May 25, 1998.

(30) Foreign Application Priority Data

May 27, 1997 (DE) .......................... 197 22 063

(51) Int. Cl.[7] .............................................. A61B 17/00
(52) U.S. Cl. ........................ 606/1; 606/41; 606/46
(58) Field of Search ................................. 606/1, 41, 45, 606/46, 48, 52

(56) References Cited

U.S. PATENT DOCUMENTS

| | | | |
|---|---|---|---|
| 4,003,380 A | 1/1977 | Wien ........................... | 128/303 |
| 4,512,343 A | 4/1985 | Falk et al. ................... | 128/303 |
| 5,312,401 A * | 5/1994 | Newton et al. ............... | 606/46 |
| 5,618,304 A | 4/1997 | Hart et al. ................... | 606/205 |
| 5,618,308 A | 4/1997 | Holmes et al. .............. | 606/205 |
| 5,766,167 A * | 6/1998 | Eggers et al. ................ | 606/46 |

FOREIGN PATENT DOCUMENTS

| | | |
|---|---|---|
| DE | P2502863 | 7/1976 |
| DE | 3217105 C2 | 8/1985 |
| DE | 4236394 A1 | 5/1994 |
| DE | 19722063 C2 | 7/1999 |
| EP | 06858333 A1 | 12/1994 |
| FR | 75 27516 | 9/1975 |
| WO | WO 98/53749 | 12/1998 |

OTHER PUBLICATIONS

Handgriffe, Scheren Bipolar–Zangen, Jan. 1994, 6 pages.

* cited by examiner

*Primary Examiner*—Michael Peffley
(74) *Attorney, Agent, or Firm*—St. Onge Steward Johnston & Reens LLC

(57) ABSTRACT

A protective cap for a medical high-frequency instrument is configured such that it covers the high-frequency instrument in insulating fashion at least in the vicinity of an electrical connector for a high-frequency cable.

19 Claims, 3 Drawing Sheets

PROTECTIVE CAP FOR MEDICAL HF INSTRUMENTS

CROSSREFERENCE OF PENDING APPLICATION

This application is a continuation of pending international application PCT/EP98/03064 filed on May 25, 1998

BACKGROUND OF THE INVENTION

The present invention relates to a protective cap for medical HF instruments.

HF (high-frequency) instruments are commonly known, and are presented, for example, in the catalog of the company styled Karl Storz GmbH & Co., "Endoskopische Chirurgiell" [Endoscopic surgery], Section 6, 2nd ed. 1/94.

HF instruments are used for high-frequency coagulation or for high-frequency cutting.

High-frequency coagulation is used for surgical destruction of tissue areas, for hemostasis, to remove portions of tissue, or for thermal coagulation of tumors.

High-frequency cutting can be performed with HF instruments of the same design as for high-frequency coagulation high-frequency cutting is used, for example, to remove cysts, to cut through vessels, or for similar surgical interventions.

For use in the widely practiced technique of minimally invasive surgery, HF instruments are configured as tubular-shaft instruments.

Tubular-shaft instruments comprise a proximal handle and a shaft, joined immovably or detachably thereto, that is configured as a tubular shaft. Guided through this tubular shaft is a working insert that, at its distal end, projects beyond the shaft and carries the actual working device, for example a needle-shaped electrode or the mouth parts of a cutting or grasping tool.

The current to be applied is delivered via a high-frequency cable from a high-frequency generator arranged remotely from the HF instrument. For electrical connection to the instrument, a connector is provided on it. This connector usually comprises a metal pin mounted on the handle of the instrument and protruding from it.

The connector is in electrical contact with the actual working device, so that the current is guided through it to the distal end.

Whereas the connector for the high-frequency cable is generally immovably joined to the HF instrument, the generator is connected to the HF instrument, via the cable, only as necessary.

A distinction is made between unipolar and bipolar HF instruments, depending on the type of current delivery.

In a unipolar (also called monopolar) HF instrument, a connector for only one pole is provided on the instrument. The patient lies on an electrically conductive mat that constitutes the second pole. The current emerging from the distal end of the unipolar HF instrument flows over a large area through the patient's body to the conductive mat.

In bipolar HF instruments, two connectors are present on the instrument, i.e. the current is fed in at the proximal end, delivered to a tool (e.g. a coagulation loop) at the distal end, then returned back to the proximal end and there discharged.

The term "connector" hereinafter comprises, in the case of mono- or unipolar HF instruments one connector, and in the case of bipolar HF instruments two connectors or connector plugs.

It has been found in practical use that electrical arcs can occur in the region of the connector plug, resulting in jerky reactions on the part of the surgeon. Adverse effects can also result from leakage currents.

A variety of solutions have hitherto been proposed for protecting the surgeon from such adverse effects.

For example the aforementioned catalog of Karl Storz GmbH & Co. shows, in Section 5 on page SCT 5/1 A, a handle for a tubular-shaft instrument having a connector for a unipolar high-frequency cable, in which insulation is achieved by the fact that the handle is made substantially of nonconductive plastic. Only the connector pin is made of metal, and is insert molded into the plastic. The handle has one fixed and one movable handle element, which can be moved relative to one another by way of a hinge joint made of plastic.

This type of insulation has the disadvantage that the handles do not exhibit sufficient mechanical stability.

The plastic hinge that was used could not withstand the mechanical stresses.

The pivot pins were therefore once again made of metal.

Since, however, the joints are located in close proximity to the connector for the high-frequency cable, the risk once again exists of voltage arcing or leakage currents from the connector to the metal hinge pin.

Because of the poor mechanical stability of plastic handle elements for HF instruments, it was alternatively proposed to utilize metal parts and to cover them with an electrically insulating plastic coating.

These coatings have not, however, proven durable over the long term. Handling, especially during cleaning and autoclaving, creates the risk that the coating can become damaged and can detach, and thereby expose metal areas of the instrument. In particular, a coating can exhibit less than complete coverage in areas where moving parts make contact with one another, for example at joints. This can result in arcs or leakage currents during HF use.

The purpose of the handle at the proximal end of the instrument, on which the connector for the high-frequency cable is present, is to control the distal end of the working device, e.g. spreadable mouth parts, extending through the tubular shaft.

For this purpose, an actuation element, usually in the form of a rod, projects proximally beyond the tubular shaft and is joined to a movable handle element of the handle. When the handles are, as is usual, scissor-like, one end of the handle element that is movable (i.e. pivotable) about the hinge axis is mechanically connected to the proximal end of the actuation element projecting beyond the tubular shaft, in order to convert a pivoting movement of the handle element into a linear displacement movement of the rod-shaped actuation element.

Ball-and-socket joints have proven successful as the mechanical connection, especially for instruments that can be disassembled. The usually solid, proximally projecting end of the metal actuation element is located, depending on the design, in the vicinity of the connector for the HF cable, and during HF operation also constitutes an exit point for arcs. Even insulation of this area cannot provide a remedy, since any insulation would soon be rubbed off by the frictional ball-and-socket mechanism.

With bipolar HF instruments, there exists the additional risk of arcing from the connector plug of the one pole to the connector plug of the other pole.

Against this background, it is the object of the present invention to create a reliable insulation system for HF instruments that does not adversely affect the stability and functionality of the other components of the HF instrument.

SUMMARY OF THE INVENTION

According to the present invention, the object is achieved by a protective cap which is configured such that it covers the instrument in insulating fashion at least in the vicinity of an electrical connector for a high-frequency cable.

This object is furthermore achieved by a medical HF instrument that has a protective cap of this kind.

The provision of an insulating protective cap eliminates the absolute necessity either for the HF instrument, or at least those regions of the HF instrument in which the connector for the high-frequency cable is located, to be produced entirely from insulating material; or, in the case of metallic materials, for them to be completely equipped with an insulating covering. For example, the handle including its joint and the connector for the high-frequency cable can be produced from metal, and nevertheless protected, in optimally electrically insulating fashion, against arcing once the protective cap has been attached. The protective cap thus makes it possible to manufacture those components that contain the electrical connector from mechanically stable and resistant material. Since the protective cap covers at least the vicinity of the electrical connector in insulating fashion, the danger of arcing or leakage currents to conductive elements and thus to the surgeon is eliminated. The electrical connector as such is, of course, electrically insulated with respect to the handles.

Depending on whether the instrument is configured as a unipolar or bipolar instrument, one connector plug or two connector plugs and their vicinity are covered in insulating fashion.

The protective cap can be manufactured as a relatively economical component from any material having good electrical insulation. When it is produced as a plastic injection-molded part, it can, for example, be designed for one-time use.

The HF instrument can thus be manufactured from suitable mechanically stable materials with no consideration of insulation against arcing in the region of the connector, since this is now accomplished by the protective cap that can be put in place subsequently or as required.

In a further embodiment of the invention, current-carrying components in the vicinity of the connector that are exposed, or that become exposed due to actuation of the HF instrument, are also covered by the protective cap.

This feature has the considerable advantage of ensuring, in all possible operating and handling positions, that not only exposed metal parts but also metal parts that become exposed during handling are covered. In the case of the aforementioned ball-and-socket joint connection between the actuation element in the tubular shaft and the handle element, a segment of greater or lesser length, depending on the pivot position of the handle element, is pulled proximally out of the shaft. Since the actuation element is at the same time utilized for electrical conduction to the distal end, it is necessarily manufactured from metallically conductive material and constitutes an exit point for arcs or leakage currents. The result is therefore to ensure that not only arcing from the electrical connector, but also adverse effects resulting from the proximally projecting metallically conductive actuation element, are eliminated.

In a further embodiment, the protective cap can be placed onto the HF instrument.

This feature has the advantage that the protective cap can be put in place only when needed, i.e. during HF operation, and otherwise the instrument can be used without the protective cap.

In a further embodiment of the invention, the protective cap can be placed onto a handle that has handle elements joined via a hinge joint, the protective cap extending over the hinge joint.

The advantage of this feature is that the hinge joint, regardless of whether the remaining handle elements are manufactured from plastic material or other materials, can comprise a metal pin, which contributes greatly to the mechanical stability of the handle and the joint. The protective cap proceeds from the connector and extends over the region of the joint, so that arcing to the metal joint pin is ruled out.

In a further embodiment of the invention, the shape of the protective cap is adapted to the contour of those parts of the HF instrument onto which it is placed.

The advantage of this feature is that the protective cap, once put in place, conforms closely to the contour of the HF instrument and does not constitute a bulky component that interferes with the surgeon. This rules out any need for the surgeon to grip the HF instrument differently, because the protective cap is in place, than in non-HF operation without the protective cap, thus enhancing handling ease and operating reliability.

In a further embodiment of the invention, the shape of the protective cap is configured such that movement of the handle elements in the region of the protective cap is possible without being limited thereby.

The advantage of this feature is that the protective cap covers the entire movement range of the handle elements, i.e. sufficient insulation is ensured in every handle element position, while at the same time the freedom of movement of the handle element is not limited despite the presence of the protective cap.

In a further embodiment of the invention, the protective cap can be slid onto a connector for a high-frequency cable that is joined immovably to the HF instrument and protrudes therefrom.

The advantage of this feature is that the cap can be slid over the connector onto the instrument in securely guided fashion. This procedure can be performed easily, quickly, and without close attention. A corresponding opening can be provided in the cap, through which the connector, protruding from the instrument, passes as it is slid on, so that the slid-on cap can then directly surround and cover the connector and therefore the principal source of the arcing hazard is insulated in particularly secure fashion.

In a further embodiment of the invention, the protective cap has a tubular extension that can be slid over a pin-shaped connector protruding from the HF instrument.

The advantage of this feature is that the cap, guided by the tubular extension, can be slid in directed fashion into a specific position on the HF instrument.

In a further embodiment of the invention, an attachment element is provided with which the protective cap can be secured on the HF instrument.

The advantage of this feature is that the protective cap is secured in particularly reliable and lossproof fashion, so that it cannot slip or become detached even if the HF instrument is set down between multiple treatment procedures.

In a further embodiment of the invention, the protective cap is made of an electrically insulating plastic material.

The advantage of this feature is that the protective cap can be manufactured from an economical material that can be manufactured, for example, using the injection-molding method, and thus can be designed as a disposable part for one-time use.

In a further embodiment of the invention, the protective cap is made of a ceramic material, e.g. an oxide ceramic or a glass ceramic.

The advantage of this feature is that a material that is not only insulating but also extremely mechanically strong is present, so that the protective cap can withstand even a large number of cleaning and autoclaving procedures.

In a further embodiment of the invention, the protective cap can be placed onto the HF instrument in detachable fashion.

The advantage of this feature is that the cap can be removed, either for cleaning or if the instrument is no longer being used in HF mode.

In a particular embodiment of the invention, the protective cap can be placed onto an HF instrument in which a handle is joined to a tubular shaft element via a releasable snap-lock connection, an actuation knob being present for closing and releasing the snap-lock connection, said knob being utilized to secure the protective cap.

The considerable advantage of this feature in this specific case is that attachment of the protective cap can be simultaneously accomplished using a component already present on the HF instrument. For the cleaning process, the instrument can be disassembled in such a way that the protective cap is present as an individual part, and can be cleaned correspondingly.

In a further embodiment of the invention, the protective cap itself has a connector for a high-frequency cable, and after placement onto an HF instrument, the connector is connected to a conductive part of the HF instrument.

This feature has the advantage that the connector, which is usually configured as a metal connector pin, is integrated into the protective cap, so that provision is already made during manufacture for a correspondingly insulated connection between these two components. Once the protective cap is put in place, the connector integrated into it creates the electrical connection between the HF connector cable and the conductive component of the HF instrument. In the case of a bipolar HF instrument, two connector plug pins are present.

In a further embodiment of the invention, provision is made for handling features, which facilitate placement or removal of the protective cap, to be present on the protective cap.

The advantage of this feature is that a replacement operation can be performed easily and reliably.

In a further embodiment of the invention, the handling features comprise grip elements, grip ribs, a shaped-on handle, or a roughening.

These features on the one hand are very easy to carry out in terms of production engineering, especially in the case of a configuration as an injection-molded part; and on the other hand they constitute unequivocal handling features for the fingers of a human hand, so that secure grasping and removal or placement are possible even without close attention, and in particular without direct visual contact.

In a further embodiment of the invention, the protective cap can be mounted onto the HF instrument and pulled off from it only when the grip elements are in a specific position.

The advantage of this feature is that the grip elements constitute a specific securing means for the protective cap with no necessity for an additional operating element for the purpose.

In a further embodiment of the invention, the protective cap is joined to the high-frequency cable.

The advantage of this feature is that the protective cap becomes part of the plug connector.

It is understood that the features mentioned above and those yet to be explained below can be used not only in the respective combination indicated, but also in other combinations or in isolation, without leaving the context of the present invention.

BRIEF DESCRIPTION OF THE DRAWINGS

The invention will be described and explained below with reference to a few selected exemplary embodiments in conjunction with the appended drawings, in which.

DETAILED DESCRIPTION OF PREFERRED EMBODIMENTS

Figure 1:
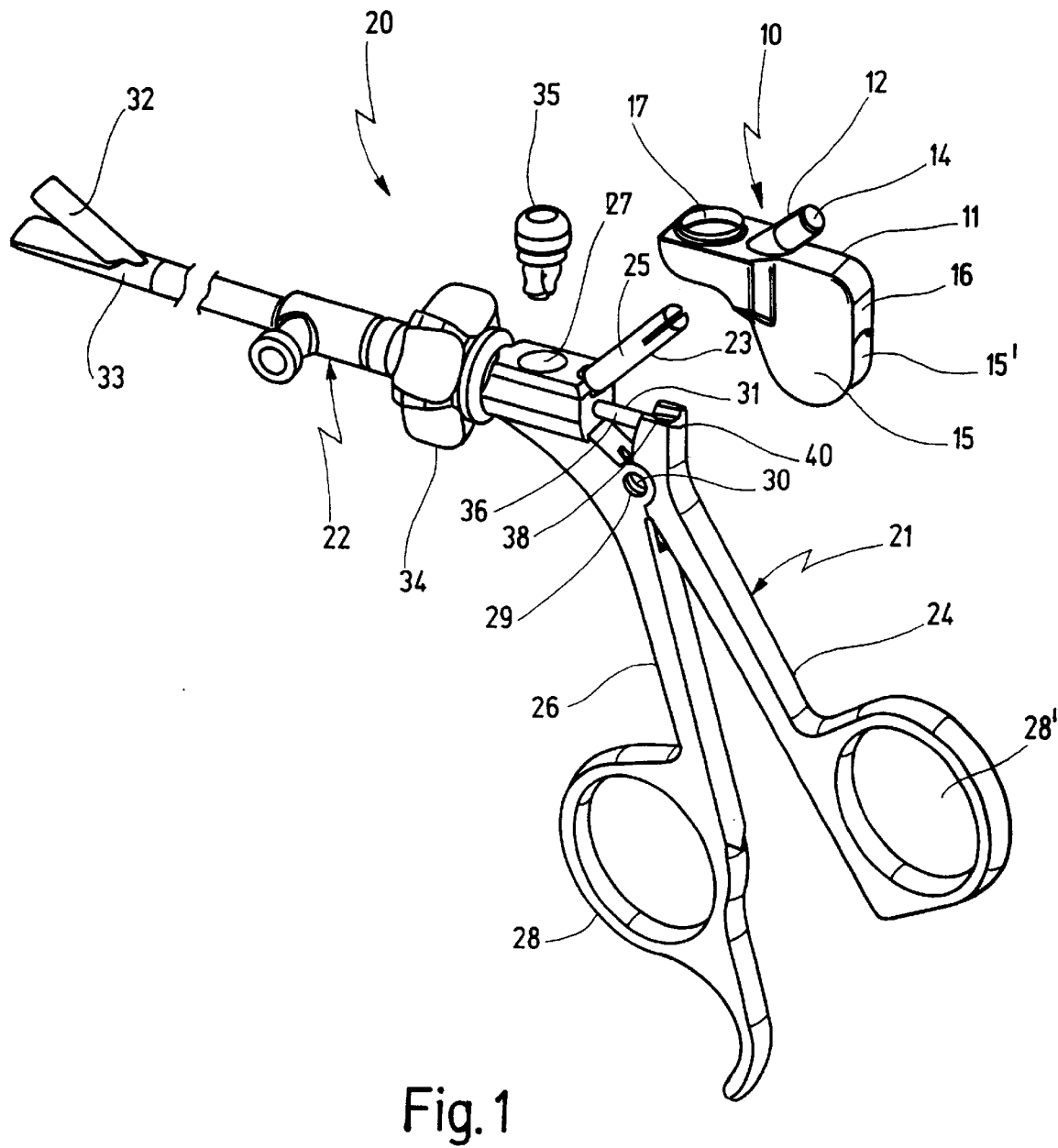
FIG. 1 shows a perspective exploded view of an HF instrument and a protective cap that has not yet been put in place.

A protective cap 10 shown in FIG. 1 has a housing 11 from which a tubular extension 12 projects.

Housing 11 has two sidewalls 15, 15' that are joined to one another by a crosswall 16.

Crosswall 16 extends over a top region (in the representation of FIG. 1) and a portion of the rear proximal region.

Extension 12, which is inclined approximately 45° with respect to the crosswall surface, extends from the upper region of crosswall 16.

An opening 17 is also provided in crosswall 16 on the upper side. Opening 17 serves to receive an attachment element, to be described later, with which protective cap 10 can be secured to an HF instrument 20.

Protective cap 10 is manufactured from an electrically insulating oxide ceramic.

Figure 2:
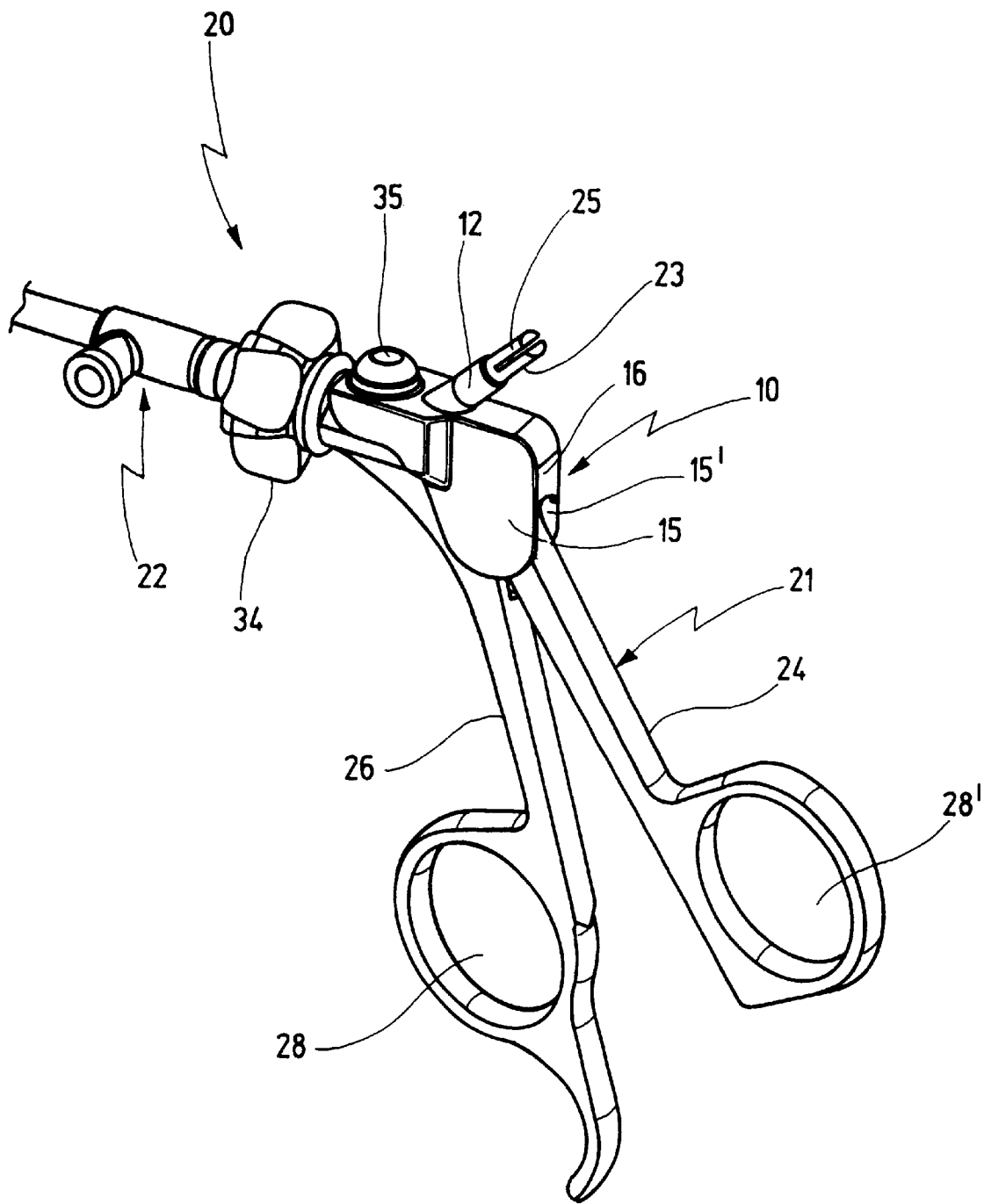
FIG. 2 shows a view, corresponding to the FIG. 1, with the protective cap put in place on the HF instrument.

The unipolar HF instrument shown in FIGS. 1 and 2 is a tubular-shaft instrument having a handle 21 and a tubular shaft 22 detachably joined thereto.

Handle 21 comprises a movable handle element 24 and a fixed handle element 26.

Fixed handle element 26 is detachably joined to the proximal end of tubular shaft 22.

Projecting upward at an angle of 45° from fixed handle element 26 at the proximal end is a connector 23 in the form of a metal connector pin 25.

Movable handle element 24 and fixed handle element 26 are joined to one another via a hinge joint 30.

A joint pin 29 of hinge joint 30 constitutes the joint axis about which movable handle element 24 can be pivoted relative to fixed handle element 26.

Both handle elements 24 and 26 are equipped with finger loops 28, 28'.

A rod-shaped actuation element 31, which projects beyond tubular shaft 22 at the distal end and carries two mouth parts 33 and 34, is received in tubular shaft 22.

At the proximal end, a segment 36 of actuation element 31 projects beyond the proximal end of fixed handle element 26. Segment 36 is equipped at the end with a ball 38 that is received in a corresponding socket 40 at the upper end of movable handle element 24.

Pivoting of movable handle element 24 about hinge joint 30 results in a linear displacement of actuation element 31, and thus in opening or closing of mouth parts 32, 33.

An adjusting wheel 34 on fixed handle element 26 serves to rotate tubular shaft 22, together with actuation element 31, about the tubular shaft axis.

A knob 35 serves to lock tubular shaft 22 in axially nondisplaceable fashion.

Pin 25, projecting at an angle of approximately 45° from the upper end of fixed handle element 26, can pass through interior 14 of tubular extension 12 of protective cap 10.

In order to place protective cap 10 onto unipolar HF instrument 20, it is oriented as shown in the exploded representation in FIG. 1, then slid on in such a way that pin 25 passes through tubular extension 12.

Once protective cap 10 has been completely slid on (see FIG. 2), its opening 17 coincides with that opening 27 into which knob 35 is to be threaded with the aid of a special tool (collet chuck).

Knob 55 can then first be pushed from the outside through opening 17 in protective cap 10, and then inserted into opening 27 and locked therein. This ensures that protective cap 10 is seated in detachable but nondisplaceable fashion.

As is evident from FIG. 2, pin 25 projects beyond tubular extension 12, so that an HF cable can be placed onto this projecting segment.

It is also evident from the representation of FIG. 2 that the spacing of sidewalls 15, 15' is such that handle elements 24 and 26 just fit between them.

Because crosswall 16 does not extend, on the proximal side, all the way to the lower end of protective cap 10, movable handle element 24 can be moved back and forth without limitation even though protective cap 10 is in place.

The extension of sidewalls 15, 15', viewed in the direction from connector 23 toward finger loops 28, is such that hinge joint 30 is completely covered. As a result, it is not possible for arcing to take place from connector 23 onto the hand of a person who has grasped the handle elements. Handle elements 24 and 26 can be manufactured either from an insulating plastic or from a metallic material covered with an insulating plastic coating.

It is apparent from the representation of FIG. 2 that crosswall 16 covers, as the upper end, the region of segment 36 of actuation element 31 in which the latter projects proximally beyond fixed handle element 26.

Connector 23 is connected in electrically conductive fashion to actuation element 31, since electric current is conducted through it to the distal end and to mouth parts 32 and 33.

As a result of this configuration and geometry of protective cap 10, in HF operation arcing cannot occur either from connector 23 or from the projecting segment 36 onto metal pin 29, since the latter is covered in insulating fashion by protective cap 10.

Figure 3:
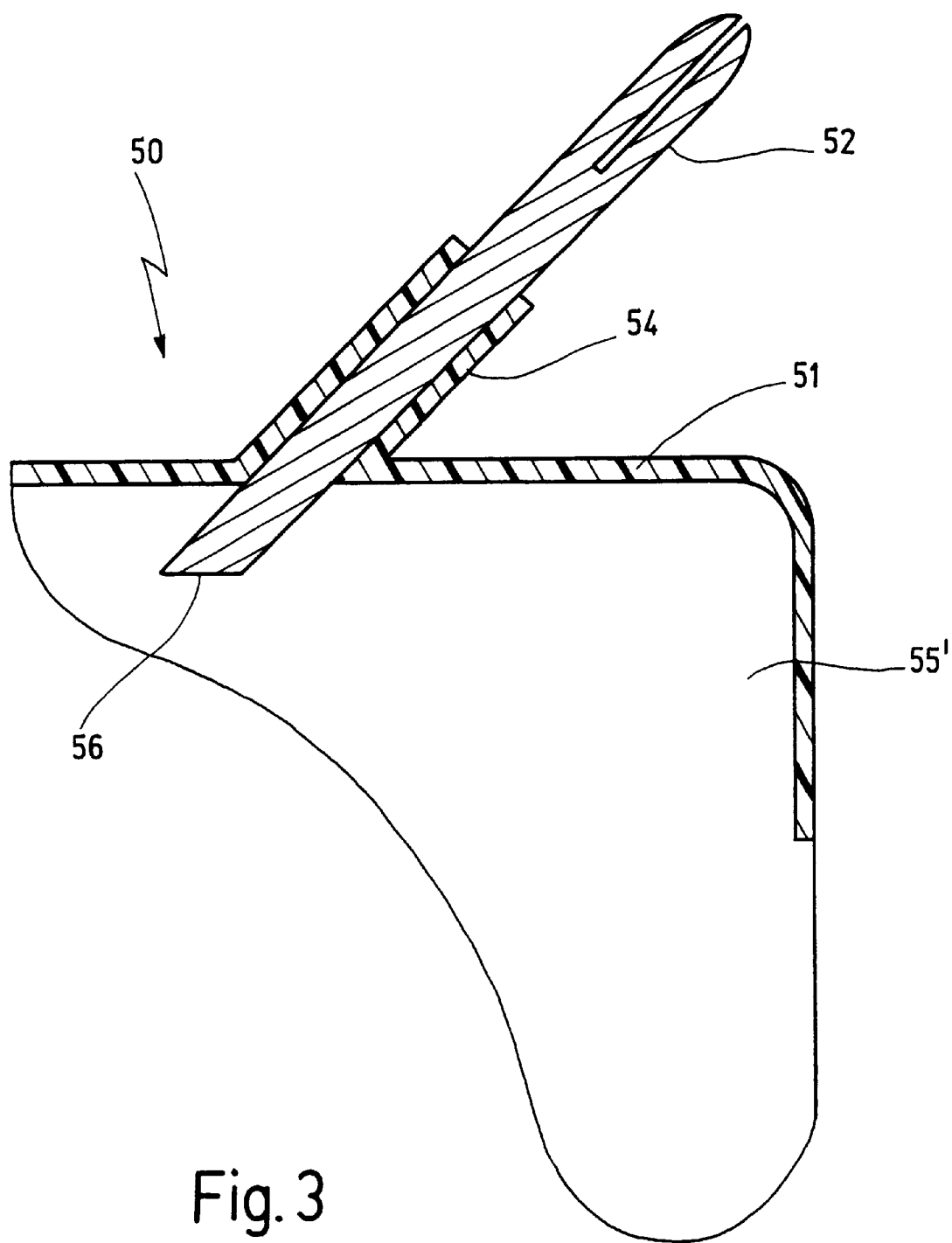
FIG. 3 shows a longitudinal section of a further embodiment of a protective cap with an integrated connector for an HF cable.

FIG. 3 schematically shows a longitudinal section of a further exemplary embodiment of a protective cap 50.

The contour of protective cap 50 is similar to the contour of protective cap 10 described earlier; a tubular extension 54 projecting from upper crosswall 51 carries a metallic connector pin 52. An end 56 of the connector pin projecting into the interior of protective cap 50 serves to make electrical contact with the actuation element, after protective cap 50 has been placed onto an HF instrument.

In contrast to the exemplary embodiment presented earlier, connector pin 52 is an integral constituent of protective cap 50. In the case of a bipolar HF instrument, two connector pins are provided.

In contrast to the embodiment of protective cap 10 presented earlier, the spacing of sidewalls 15, 15' is selected so that they can be slid with an exact fit, overcoming a certain frictional resistance, onto stationary handle element 26. Additional snap-lock or clip devices can then also be provided.

What is claimed is:

1. A combination of a medical high-frequency instrument and a protective cap for an insulating protective covering of said medical high-frequency instrument, said high-frequency instrument having an electrical connector for connecting that high-frequency instrument to a high-frequency cable, said high-frequency instrument having current-carrying components in a vicinity of said connector, which components may become exposed due to actuation of said high-frequency instrument, wherein said protective cap has a shape in that it covers said high-frequency instrument in an insulating fashion at least in said vicinity of said electrical connector, thereby also covering said components which may become exposed due to actuation of said high-frequency instrument, said protective cap can be slipped onto said high-frequency instrument if desired, and wherein said cap can be slipped onto a handle of said high-frequency instrument, said handle has handle elements joined via a hinge joint, and wherein said protective cap extends across said hinge joint.

2. The combination of claim 1, wherein said shape of said protective cap is configured in such that a movement of said handle elements is possible without being limited by said protective cap.

3. The combination of claim 1, wherein said shape of said cap is adapted to a contour of a region of said high-frequency instrument onto which region said cap is slipped on.

4. The combination of claim 1, wherein a shape of said cap is in that said cap can be slid onto said connector for said high-frequency cable, which connector is joined immovably to said high-frequency instrument and protrudes therefrom.

5. The combination of claim 4, wherein said cap is provided with a tubular extension, which extension is provided for being slipped onto said connector.

6. The combination of claim 1, wherein a locking element is provided for locking said protective cap with said high-frequency instrument.

7. The combination of claim 1, wherein said cap is made of an electrically insulating plastic material.

8. The combination of claim 1, wherein said cap is made of a ceramic material.

9. The combination of claim 1, wherein said cap can be slipped onto said high-frequency instrument in a detachable manner.

10. The combination of claim 1, wherein for slipping said cap onto said high-frequency instrument having a handle joined to a tubular shaft element via a snap-lock connection, said protective cap can be secured to said high-frequency instrument via a knob for releasing said snap-lock connection.

11. The combination of claim 1, wherein said protective cap is provided with a connector for a high-frequency cable, and wherein, after slipping on said protective cap onto said high-frequency instrument, said connector of said protective cap is conductively connected to a conductive part of said high-frequency instrument.

12. The combination of claim 1, wherein handling features are provided for facilitating said slipping on or a removal of said protective cap.

13. The combination of claim 12, wherein said handling features comprise elements selected from the group consisting of grip elements, grip ribs, a shaped-on handle or a roughening.

14. The combination of claim 2, wherein said protective cap can be slipped onto said handle of said high-frequency instrument only if that handle elements are in a particular position.

15. The combination of claim 1, wherein said cap is joined to a high-frequency cable.

16. A protective covering for a medical instrument, comprising:
- a housing having two sidewalls adapted to vertically extending over part of a handle of the medical instrument, said two sidewalls being generally parallel to each other;
- said housing further including a cross wall for joining said two sidewalls; and
- said housing further including a top wall adapted to extending over an electrical connector of the medical instrument.

17. The protective covering according to claim 16, further comprising an opening for positioning said housing on the medical instrument.

18. The protective covering according to claim 16, said top wall and said two sidewalls further adapted to extending over a handle joint of the medical instrument.

19. The protective covering according to claim 16, said housing further comprising an extension protruding from said top wall for accommodating the electrical connector of the medical instrument.

* * * * *